United States Patent [19]
Ko

[11] Patent Number: 6,135,966
[45] Date of Patent: Oct. 24, 2000

[54] METHOD AND APPARATUS FOR NON-INVASIVE DIAGNOSIS OF CARDIOVASCULAR AND RELATED DISORDERS

[76] Inventor: Gary Kam-Yuen Ko, 24 Coatsworth Crescent, Toronto, Ontario, Canada, M4C 5P6

[21] Appl. No.: 09/071,348

[22] Filed: May 1, 1998

[51] Int. Cl.[7] ................................................ A61B 5/00
[52] U.S. Cl. ................ 600/481; 128/925; 128/DIG. 3
[58] Field of Search ................................ 600/300, 800, 600/481–485, 501–509; 128/897–899, 920–924, 925

[56] References Cited

U.S. PATENT DOCUMENTS

| | | | |
|---|---|---|---|
| 4,289,141 | 9/1981 | Cormier | 128/713 |
| 4,899,758 | 2/1990 | Finkelstein et al. | 128/672 |
| 5,054,493 | 10/1991 | Cohn et al. | 128/672 |
| 5,092,343 | 3/1992 | Spitzer et al. | 128/925 |
| 5,211,177 | 5/1993 | Chesney et al. | 128/672 |
| 5,265,011 | 11/1993 | O'Rouke | 600/300 |
| 5,276,612 | 1/1994 | Selker | 364/413.06 |
| 5,280,792 | 1/1994 | Leong et al. | 128/925 |
| 5,339,818 | 8/1994 | Baker et al. | 128/677 |
| 5,390,679 | 2/1995 | Martin | 128/672 |
| 5,400,795 | 3/1995 | Murphy et al. | 128/925 |
| 5,402,521 | 3/1995 | Niida et al. | 128/925 |
| 5,503,156 | 4/1996 | Millar | 128/672 |
| 5,533,511 | 7/1996 | Kaspari et al. | 128/925 |
| 5,542,421 | 8/1996 | Erdman | 128/633 |
| 5,590,218 | 12/1996 | Ornstein | 128/925 |
| 5,638,823 | 6/1997 | Akay et al. | 128/691 |
| 5,680,867 | 10/1997 | Shimazu et al. | 600/500 |
| 5,703,965 | 12/1997 | Fu et al. | |
| 5,730,142 | 3/1998 | Sun et al. | 600/578 |
| 5,740,270 | 4/1998 | Rutenbeg et al. | 600/300 |
| 5,799,100 | 8/1998 | Clarke et al. | 600/300 |
| 5,839,438 | 11/1998 | Graettinger et al. | 600/481 |
| 5,848,193 | 12/1998 | Garcia | |
| 5,961,467 | 10/1999 | Shimazu et al. | 600/500 |
| 5,982,917 | 11/1999 | Clarke et al. | 395/99 |

FOREIGN PATENT DOCUMENTS 0 765 630  4/1997  European Pat. Off. ........ A61B 5/022

OTHER PUBLICATIONS

Casaleggio et al., Neural Network for automatic anomalous QRS Complex Detection, IEEE, and 553–556, 1991.

Barschdorff et al., Neural Network based Multi Sensor Heart Sound Analysis, IEEE, and 303–306, 1991.

Wu et al., Computer–Aided Analysis and Classification of Heart Sounds Based on Neural Networks and Time Analysis, IEEE and 3455–3458, 1995.

Marques de Sá et al., Comparison of Artificial Neural Network Based ECG Classifiers Using Different Features Types, and 545–547, 1994.

Cagnoni et al., A Neural Network Expert System for Computer–Assisted Analysis of Blood–Pressure Data, IEEE, and 473–476, 1992.

(List continued on next page.)

*Primary Examiner*—Cary O'Connor
*Assistant Examiner*—Michael Astorino
*Attorney, Agent, or Firm*—Ridout & Maybee

[57] ABSTRACT

Apparatus and method for non-invasive diagnosis of cardiovascular and related disorders. The system establishes a correspondence between the dynamics of the wave contour of the arterial pressure pulse and the associated disease states. The system comprises an input module, a contour signal receiver, and a processing module. The input module utilizes a pressure transducer for taking a non-invasive measurement of the arterial pulse. The contour signal receiver amplifies, digitizes and normalizes the arterial pressure pulse signal. In the processing module, the normalized arterial pressure contour is subjected to wavelet analysis, which transforms the dynamics of the time series of arterial blood pressure contour into multi-resolution wavelet coefficients or signatures. The processing module includes a neural network which is trained to associate the diagnostic features of the transformed arterial pressure contour embedded in the coefficients with a disease condition. After the learning phase, the system is capable of diagnosing known cardiovascular conditions in patients.

17 Claims, 14 Drawing Sheets

OTHER PUBLICATIONS

"Identification of High Risk Patients in Cardiology by Wavelet Networks", Dickhaus H. et al., Proceedings of the 18th Annual Conference of the IEEE Engineering I Medicine and Biology Society. IEMBS, Amsterdam, Oct. 31—Nov. 3, 1996, vol. 3, Oct. 31, 1996, pp. 923/924, XP000788293.

"Application of pattern recognition and image classification techniques to determine continuous cardiac output from the arterial pressure waveform", Martin J.F. et al., IEEE Transactions of Biomedical Engineering, Oct. 1994, U.S.A., vol. 41, No. 10, pp. 913–920, XP002114963.

"Use of Neural Networks for Detection of Artifacts in Arterial Pressure Waveforms", Sebald, A.V., Images of the Twenty–First Century, Seattle, Nov. 9–12, 1989, vol. Part 6, No. Conf. 11, Nov. 9, 1989 pp. 2034–2035, XP000129676.

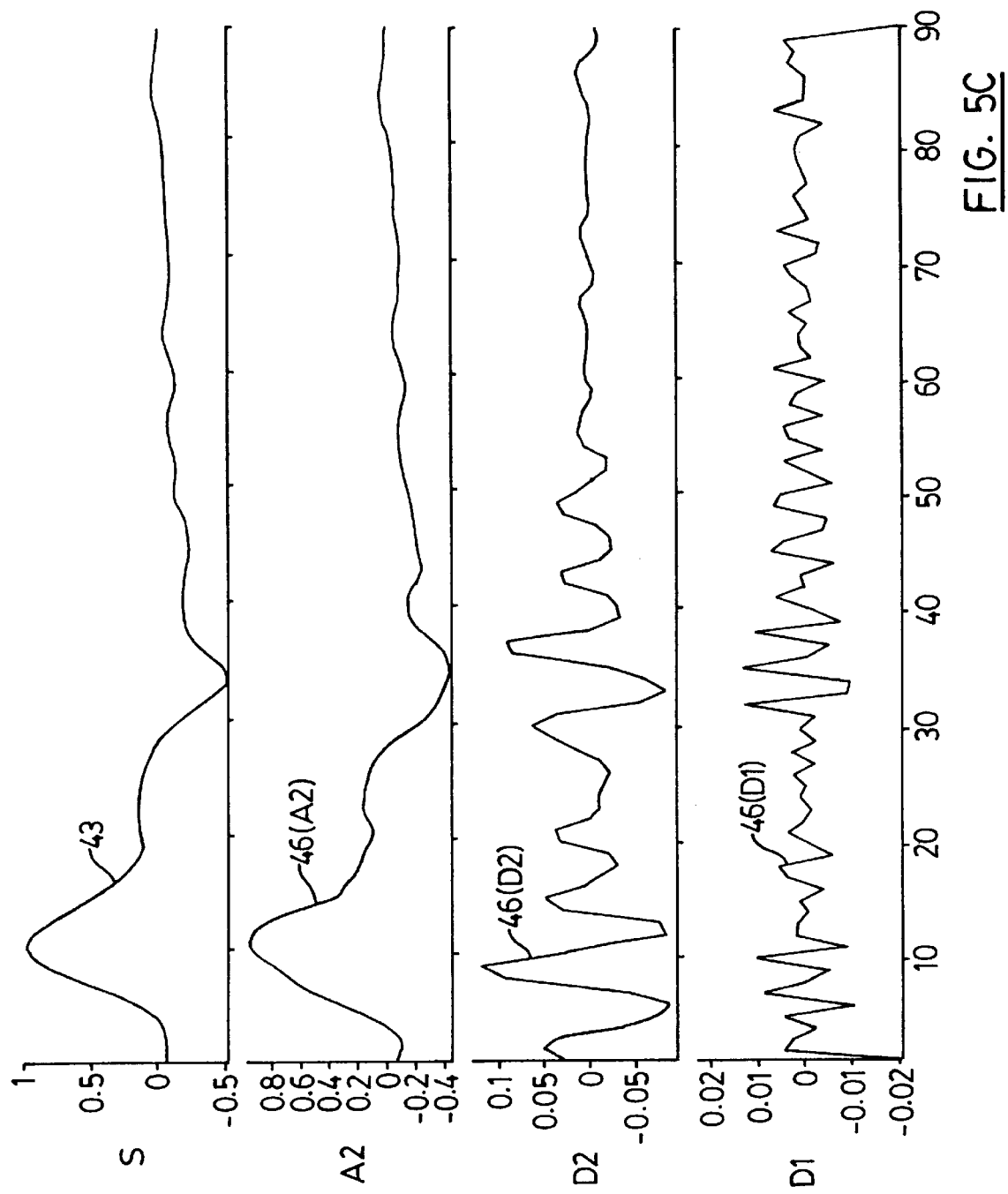

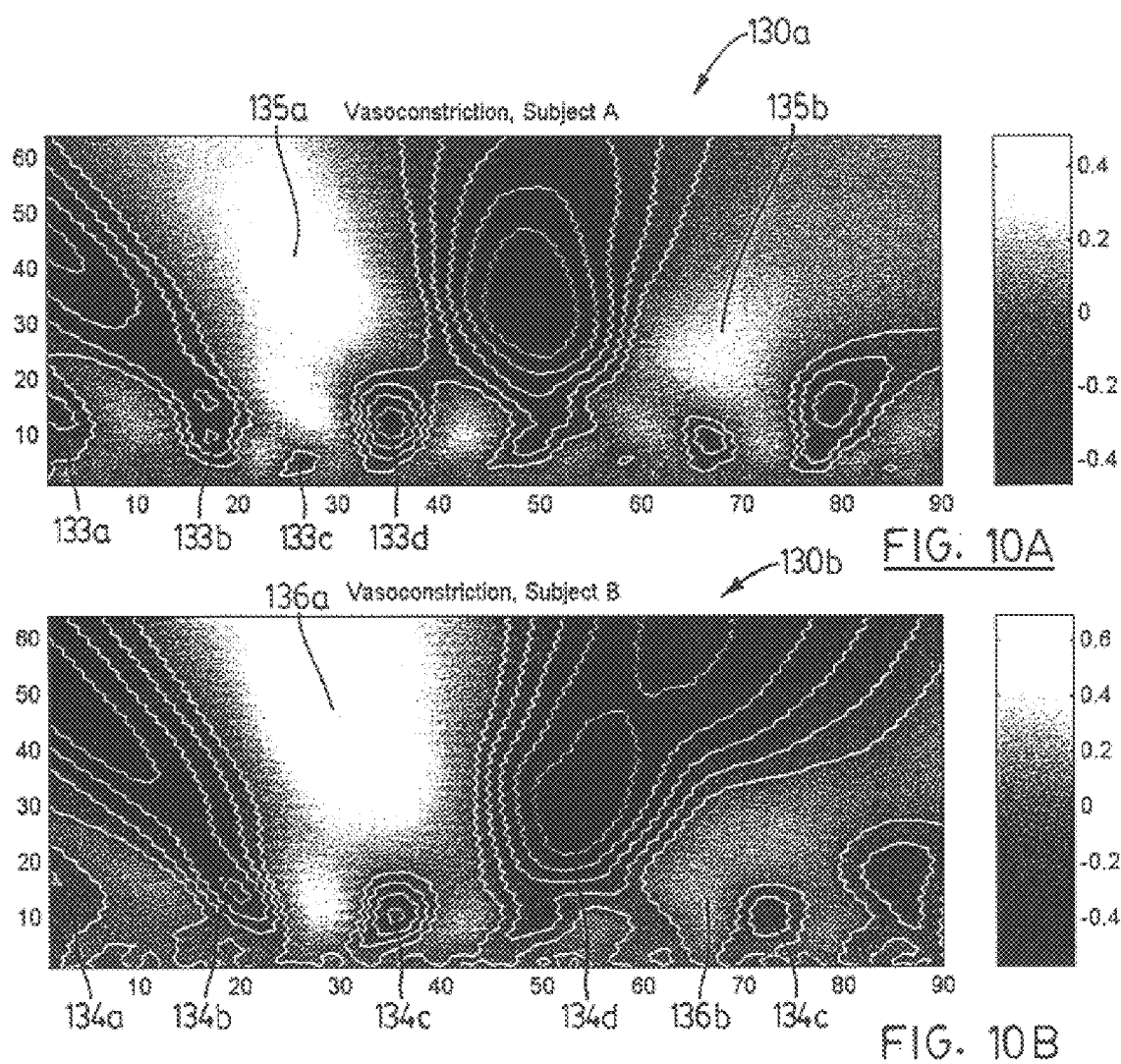

METHOD AND APPARATUS FOR NON-INVASIVE DIAGNOSIS OF CARDIOVASCULAR AND RELATED DISORDERS

FIELD OF THE INVENTION

The present invention relates to non-invasive diagnosis of cardiovascular disorders and related abnormalities. In particular, the invention relates to a method and apparatus for diagnosing cardiovascular disorders through the measurement and interpretation of the arterial pressure pulse contour.

BACKGROUND OF THE INVENTION

Methods for diagnosing cardiovascular and related disorders can be classified into one of two categories: invasive diagnostic methods, and non-invasive diagnostic methods. Invasive cardiovascular diagnostic methods are those which involve penetration of the skin or a bodily orifice. Methods of this type include the insertion of catheters and the administration of radioactive pharmaceuticals into the body. Non-invasive cardiovascular diagnostic methods do not involve penetration of the skin or a bodily orifice. Methods of this type include the administration of physical examinations, electrocardiograms, and various forms of imaging examination.

Invasive cardiovascular diagnostic methods have gained wide spread use because they have been traditionally more reliable in diagnosing cardiovascular disorders than non-invasive cardiovascular diagnostic methods. However, non-invasive cardiovascular diagnostic methods are preferable because they are usually less expensive to administer and pose less risk to the patient than do invasive cardiovascular diagnostic methods.

One particularly effective non-invasive cardiovascular diagnostic technique involves palpating the radial arterial pulse with one's fingers. This technique has been successfully employed for centuries by practitioners of traditional Chinese Medicine and many medical practitioners in other cultures, including the Greeks, East Indians, Arabians and the British. In many of these cultures, where expensive diagnostic tools may not be readily available, palpation of the radial arterial pulse has been the first and sometimes only cardiovascular diagnostic tool. This tool is also effective in diagnosing other diseases since many disease states have concomitant cardiovascular manifestations.

Palpating the radial arterial pulse as a method of diagnosing disease, including cardiovascular disease, is based on the finding that the shape or contour of the arterial pulse contains important diagnostic information concerning the physiological state of the patient. When an arterial pulse is generated centrally at the heart, the pulse propagates into all parts of the circulatory system or vasculature, and is later reflected back centrally, like a wave reflected back by the edge of a pond. The magnitude and timing of the reflection or the contour of the reflection event depends critically on the state of the blood vessels which supply different organ systems in the body. One can thus think of the centrally generated arterial pulse as a interrogating test pulse, the reflection of which contains important diagnostic information concerning the physiological state of the vasculature and the end organs it supplies. As described in M. F. O'Rouke, R. Kelly and A. Avolio, *The Arterial Pulse* (Philadelphia: Lea & Febiger, 1992), this reflected wave, together with the events associated with heart valve closures, plays a dominant role in the shaping of the arterial pulse contour.

However, the art of palpating the radial arterial pulse as a method of diagnosing cardiovascular and related diseases has not attained widespread acceptance. This may be attributed to the fact that the art does not yield quantitative results. As a result, reliable diagnoses can only be achieved by experienced practitioners of the art.

The blood pressure cuff or sphygmomanometer, which provides quantitative values of the systolic and diastolic blood pressures, has attained widespread acceptance as a method of diagnosing cardiovascular health. However, while the systolic and diastolic pressure values have been important in characterizing a patient's cardiovascular health, the systolic and diastolic pressure values do not include much of the important diagnostic information contained within the arterial pressure pulse contour. As a result, the use of sphygmomanometer as a means of diagnosing cardiovascular and related diseases is limited.

Systems have been developed to improve upon the method of diagnosing cardiovascular disease offered by the sphygmomanometer. For example, U.S. Pat. No. 5,638,823 to Akay et al. teaches a system for non-invasively detecting coronary artery disease. The system performs a wavelet transform on an acoustic signal representative of the diastolic heart sounds of the patient. The first four moments of the wavelet transform are included in a feature vector which is input into a neural network. The neural network diagnoses the presence of coronary artery disease based on the information contained in the feature vector.

However, the system taught by Akay is deficient in several respects. First, since the system analyses the acoustic turbulence associated with blood flowing in the patient's arteries, the system is capable of detecting the presence of one disease only, namely coronary arterial stenosis. Second, the system requires that the patient be administered a vasodilator drug to improve the signal-to-noise ratio of the diastolic heart sound. Therefore, the system is limited by the availability of such drugs and the allergic profile of the patient. Third, many clinical parameters, such as the patient's sex, age, weight, blood pressure and family medical history, must be included in the feature vector. As a result, the possibility of mis-diagnosis is dependent upon the accuracy of the clinical parameters input. Lastly, the system is highly susceptible to mis-diagnosis through contamination of the diastolic heart sound through other sounds such as ambient, respiratory and stomach noise.

U.S. Pat. No. 5,533,511 which issued to Kaspari teaches a method and apparatus for the non-invasive measurement of blood pressure. The method involves obtaining blood pressure pulses from a patient's blood pressure waveform by placing a piezo-electric sensor over an artery. The output pulses of the sensor are then filtered, amplified, and digitized. Time features (such as pulse amplitude, rise time, and pulse width) and frequency features (such as Fourier or Laplace transform values, phase relationships and frequency distribution) are extracted from the digitized pulses. Finally, a neural network determines the actual blood pressure of the patient based on a comparison between the extracted features and historical data acquired using blood pressure data from a plurality of patients.

However, the method taught by Kaspari is limited only to the estimation of the blood pressure pulse for clinical monitoring, and due to the nature of the Kaspari method, it is not readily adapted for the diagnosis of cardiovascular disease. Furthermore, according to the method taught by Kaspari invasive intra-arterial catheters must be used to obtain reference data of absolute blood pressure. Invasive procedures such as required by Kaspari will not be acceptable to all patients and may even pose a risk to some patients.

Accordingly, there remains a need for a method of rapidly, accurately and non-invasively diagnosing cardiovascular and related diseases.

SUMMARY OF THE INVENTION

In the present invention, there is provided a method and apparatus for rapidly and accurately diagnosing cardiovascular and related diseases, such as hardening of the arteries and general deterioration of the heart. The diagnosis can be obtained without penetrating the skin or a bodily orifice, and with minimal inconvenience to the patient. Furthermore, the speed and accuracy of the diagnosis is not limited by the skill or knowledge of the diagnostician.

The method, according to the present invention, comprises the steps of receiving a signal representative of a contour of an arterial pressure pulse; extracting frequency localization information and temporal localization information from the signal; providing the extracted information as an input to a neural network, the neural network having been trained with a plurality of training sets, each training set correlating an arterial pressure pulse contour with a known cardiovascular or related illness; and gene rating an illness identification output from the neural network.

The apparatus, according to the present invention, comprises (a) input means for receiving a signal representative of a contour of an arterial is pressure pulse; (b) information extraction means coupled to said input means for extracting frequency localization information and temporal localization information from the signal, and means for out putting a localization information output signal representing a portion of the extracted information; and (c) a neural network trained with a plurality of training sets, each training set correlating an arterial pressure pulse contour with a known cardiovascular or related illness, said neural network including means for generating an illness identification output signal representing a probability of occurrence of each known cardiovascular or related illness included in the training sets.

BRIEF DESCRIPTION OF THE DRAWINGS

Reference will now be made to the accompanying drawings which show, by way of example, a preferred embodiment of the present invention, and in which:

FIG. 5(c) shows in graphical form the decomposition of the normalized pressure contour signal of FIG. 4(c);

FIG. 10(a) shows a scale-cardiac cycle plot for a signature derived from the arterial pressure contours of FIG. 9(a) through the application of a wavelet transformation; and FIG. 10(b) shows a scale-cardiac cycle plot for a signature derived from the arterial pressure contours of FIG. 9(b) through the application of a wavelet transformation.

DESCRIPTION OF THE PREFERRED EMBODIMENTS

Figure 1:
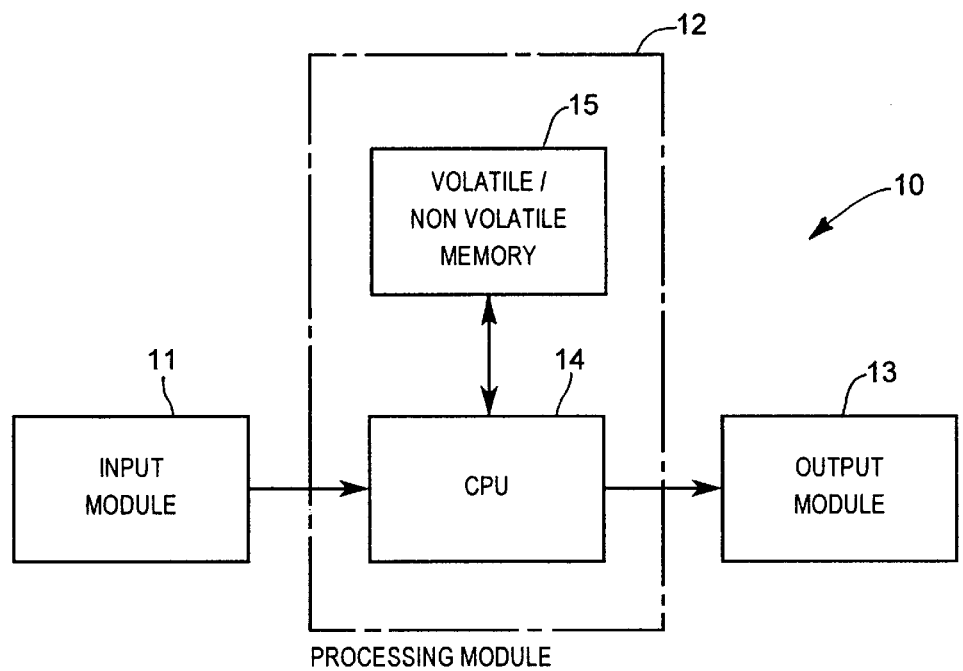
FIG. 1 is a block diagram showing a system for non-invasive diagnosis of cardiovascular disorders according to the present invention.

Reference is first made to FIG. 1 which shows in block diagram the principle modules for a non-invasive diagnostic system 10 for diagnosing cardiovascular and related illness according to the present invention. The diagnostic system 10 comprises an input module 11, a processing module 12 and an output module 13. The processing module 12 comprises a central processing unit (CPU) 14 and an arrangement of memory modules 15.

Figure 2:
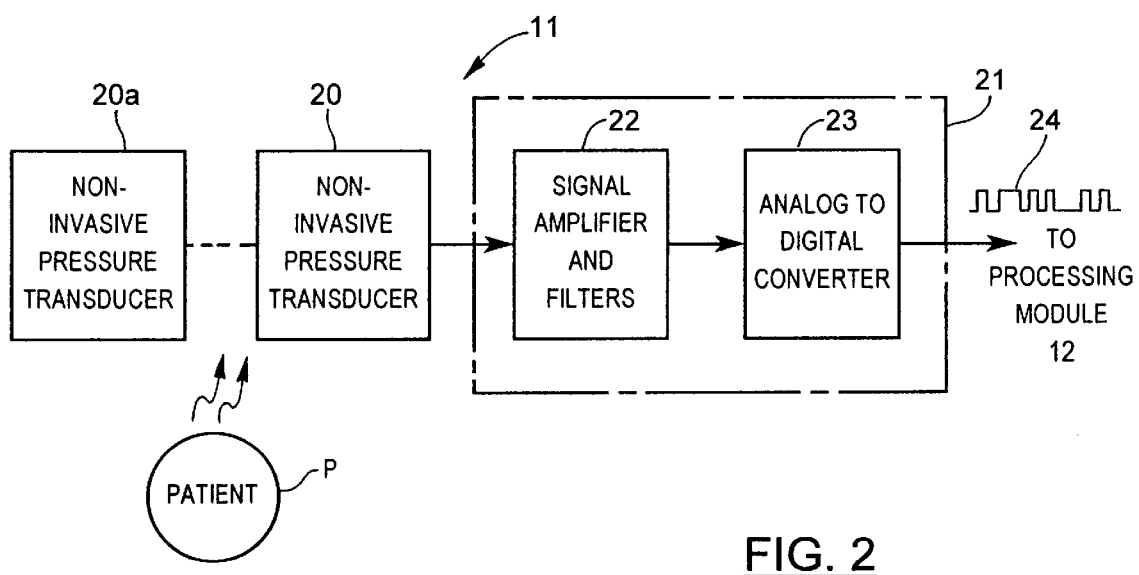
FIG. 2 is a block diagram showing in more detail the input module of the system in FIG. 1.

The input module 11 inputs contour pressure pulses from a patient or subject denoted generally by P. As shown in FIG. 2, the input module 11 comprises a pressure transducer 20 and a contour signal receiver 21 which is coupled to the output of the pressure transducer 20. The contour signal receiver 21 comprises a signal amplifier and filter stage 22, and an analog-to-digital (A/D) converter 23. The A/D converter 23 is coupled to the output of the signal amplifier and filter stage 22.

Preferably, the pressure transducer 20 is of the non-invasive type. A non-invasive pressure transducer 20 may be constructed by securing a 0.5 mm silicone membrane to trap a small volume of air over a piezo-resistive pressure sensor, such as the MPX10D available from the Motorola Corporation. The pressure transducer 20 is placed over an artery of the patient P, and then secured in place by means of an elastic strap with a Velcro™ type harness. The pressure transducer 20 detects the arterial pressure contour of the blood passing through the patient's artery, and then outputs an analog signal representative of the arterial pressure contour to the contour signal receiver 21. The pressure contour signal is then amplified and filtered by the signal amplifier and filter stage 22, and output to the analog-to-digital converter 23 in the contour signal receiver 21. The analog-to-digital converter 23 converts the pressure contour signal output into a series of digital output signals. The digital output signals provide digitized "snapshots" which define a pressure pulse signal vector 24 that is representative of the arterial pressure pulse for the patient P.

Figure 3:
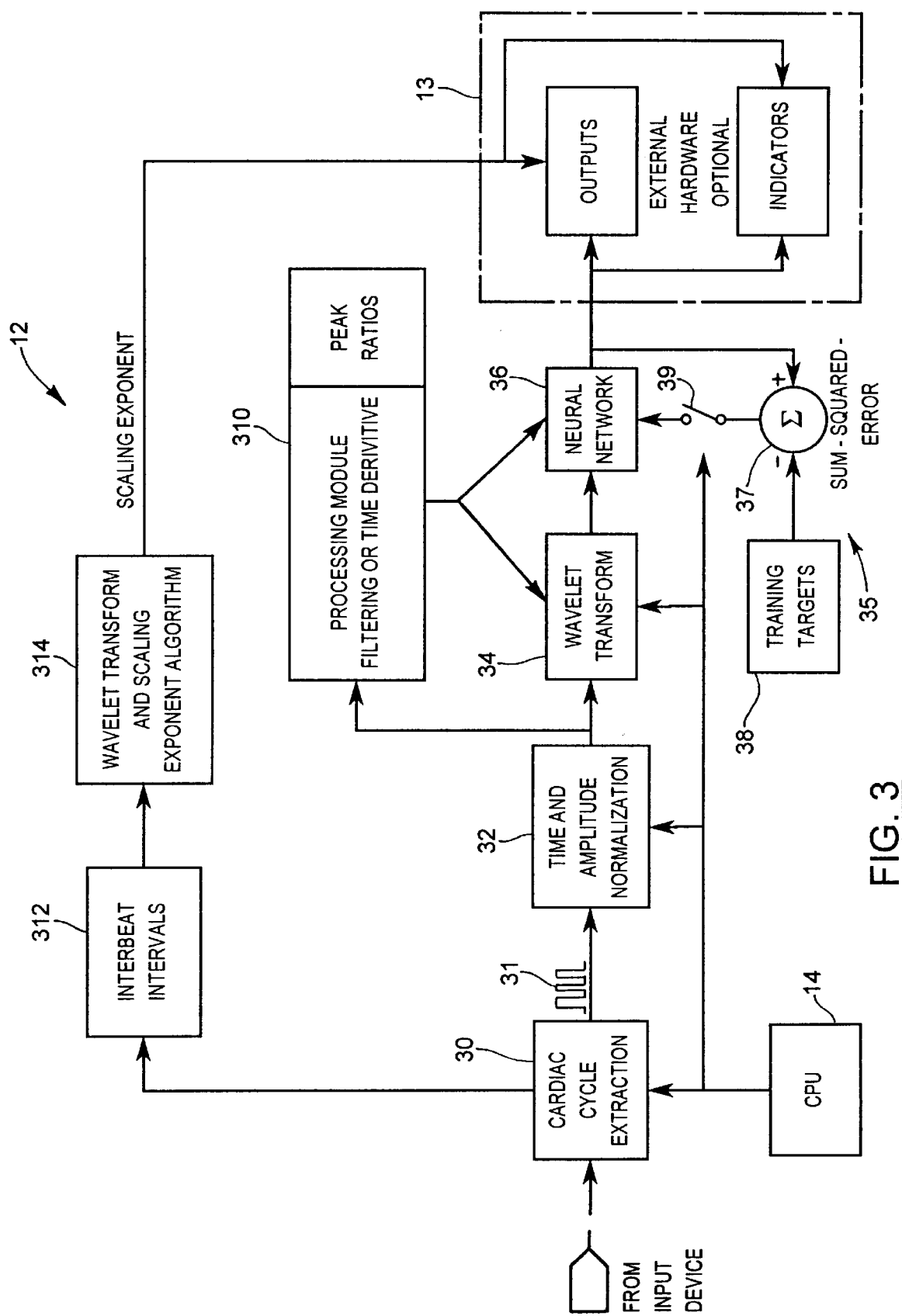
FIG. 3 is a block diagram showing in more detail the processing module and output module for the system of FIG. 1.

The pressure pulse signal vector 24 from the input module 11 is outputted to the processing module 12 (FIG. 1) for processing and analysis. As shown in FIG. 3, the processing module 12 comprises the following processing stages: a cardiac cycle extractor stage 30, a time and amplitude normalization stage 32, a wavelet transform stage 34, and a neural network stage 36. The processing module 12 also includes a training stage 35 for training the neural network 36. The operation of the training stage 35 is described below. The contour signal receiver 21 and the cardiac cycle extractor 30, time and amplitude normalization 32, wavelet transform 34, and neural network 36 stages are connected in series. The pressure pulse signal vector 24 from the contour signal receiver 21 is passed, in succession, to the cardiac cycle extractor stage 30, the time and amplitude normalization stage 32, the wavelet transform stage 34, and the neural network 36. As will be described, these elements cooperate to generate an illness identification output signal which is derived from the original arterial pressure pulse contour taken from the patient P.

Since the arterial pressure pulse is not synchronized to the wavelet transform stage 34 or the neural network 36, the pressure pulse signal vector is first received by the cardiac cycle extractor 30. Cardiac signal extractors are well known to persons skilled in the art. The cardiac cycle extractor 30 detects the systolic and diastolic peaks for each cardiac cycle, and extracts a complete pressure contour signal for each cardiac cycle of the patient. Thus, the output from the cardiac cycle extractor 30 is a pressure contour signal vector 31 which represents a complete cycle of the arterial pressure pulse contour for the patient.

Figure 4A:
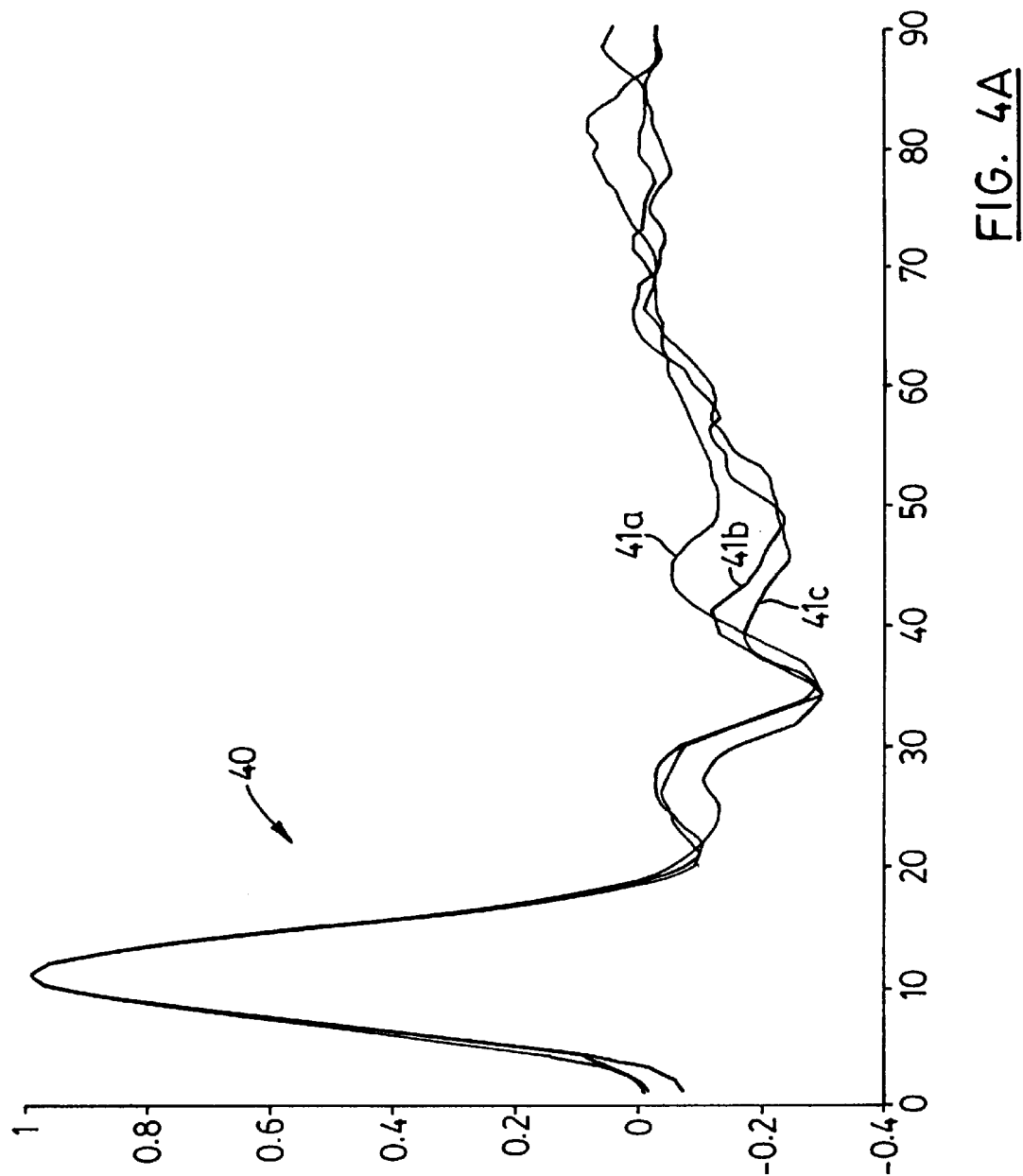
FIG. 4(a) is a graph showing normalized pressure pulse contours for a subject during normal breathing.
Figure 4B:
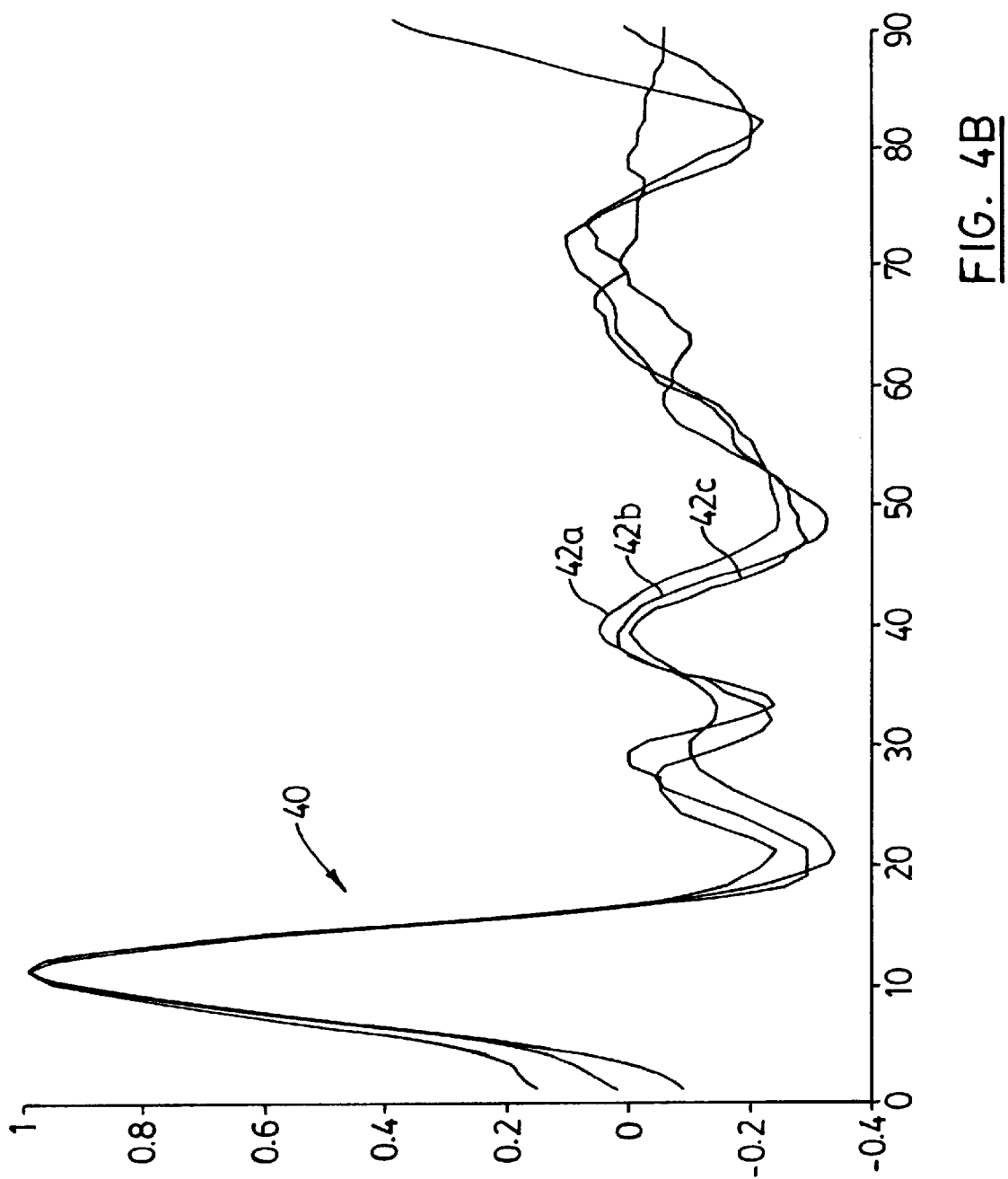
FIG. 4(b) is a graph showing normalized pressure pulse contours for a subject during a Valsalva maneuver.
Figure 4C:
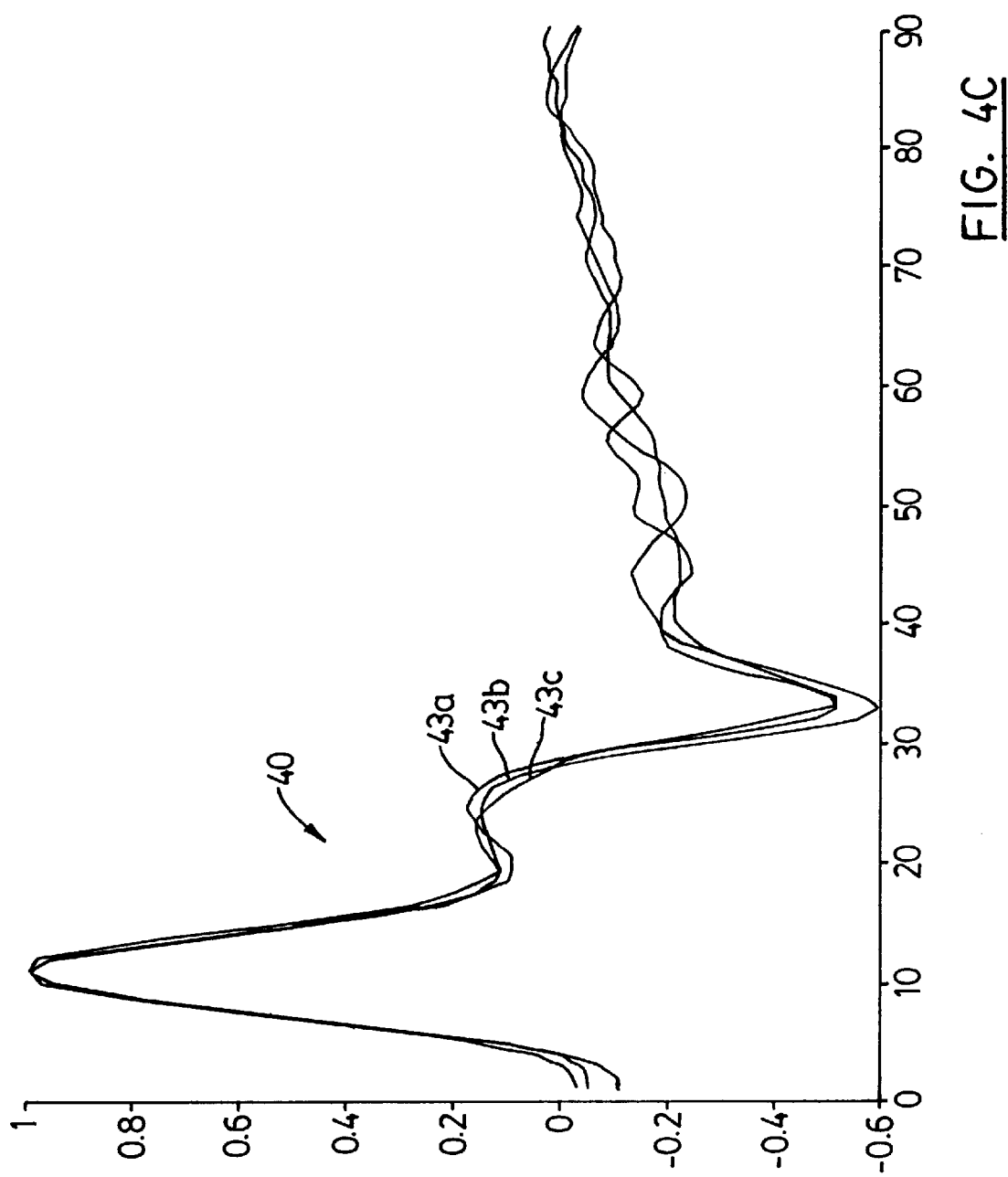
FIG. 4(c) is a graph showing normalized pressure pulse contours for a subject holding his breath.

Since the duration and amplitude of each cycle of an arterial pressure pulse contour will vary from patient to patient, the pressure contour signal vector 31 from the cardiac cycle extractor 30 is normalized by the time and amplitude normalization stage 32. The time and amplitude normalization stage 32 normalizes the duration of each cycle of the extracted pressure contour vector 31 to produce a normalized pressure pulse contour vector 40 as shown in FIGS. 4(a) to 4(c). The time and amplitude normalization stage 32 normalizes the duration of each cycle in the extracted pressure contour vector 31 so that the normalized pressure pulse contour signals 40 contain a fixed number of sample points. The amplitude of each cycle of the extracted pressure contour signal 40 is also normalized to the peak-to-peak value of each cycle. The implementation of such a time and amplitude normalization stage 32 is within the understanding of one skilled in the art.

Reference is made to FIGS. 4(a) to 4(c). FIG. 4(a) shows three exemplary normalized pressure contour signals 41, shown individually as 41a, 41b and 41c, obtained from a human subject under conditions of normal breathing. FIG. 4(b) shows three exemplary normalized pressure contour signals 42, shown individually as 42a, 42b and 42c, obtained from a human subject during the application of the known Valsalva maneuver, in which measurements are taken while the subject is strained by attempting to exhale against a close glottis. This condition mimics abnormalities in which there is a reduction of cardiac output and arterial pulse pressure (which result from a drastic increase in intra-thoracic pressure and a reduction in venous return), and an increase in sympathetic tone. FIG. 4(c) shows three exemplary normalized pressure contour signals 43, shown individually as 43a, 43b and 43c, obtained from a human subject holding their breath at the end of inspiration. This maneuver produces similar effects to the Valsalva maneuver, but to a lesser degree.

In order to detect and diagnose the cardiovascular or related illness from the arterial pressure contour, it is preferable to characterize the normalized pressure contour signal output vector of the time and amplitude normalization module 32 (FIG. 3) in detail but with a minimal number of parameters. For this task, the traditional Fourier transform is inadequate. It will be appreciated that the traditional Fourier transform works well where the signal to be characterized is composed of a few stationary components, for example, sine and cosine functions. Since the sine and cosine basis functions in the Fourier transform are localized in frequency, if the signal to be characterized includes any abrupt changes, the signal will spread out over the whole frequency axis when transformed to the frequency domain. Furthermore, the pressure pulse contours 40 (FIG. 4) will include transient events such as valve closures and wave reflections. Since the basis functions of the Fourier transform are not localized in space, traditional Fourier analysis of a pressure pulse contour would make localization of sharp and abrupt transients difficult.

Accordingly, in its preferred embodiment, the non-invasive diagnostic system 10 according to the present invention utilizes a wavelet transform for processing the normalized pressure pulse contour signals 40 (FIG. 4). The wavelet transform is implemented and performed by the wavelet transform stage 34 shown in FIG. 3. The wavelet transform comprises a known transform as described in *Wavelets and Filter Banks,* by G. Strang and T. Nguyen, and published by Wellesley-Cambridge Press, Wellesley, Mass. 1996, and will be within the understanding of those skilled in the art. In contrast to the Fourier transform, the basis functions of the wavelet transform are localized in both space and frequency or scale. As a result, many functions will be sparse when transformed to the wavelet domain. Furthermore, rather than being limited to using only sine and cosine functions, wavelet transforms have an infinite set of possible basis functions, and each can be of varying length. Accordingly, it is possible to both isolate signal discontinuities and obtain detailed frequency analysis using wavelet transforms.

Figure 5A:
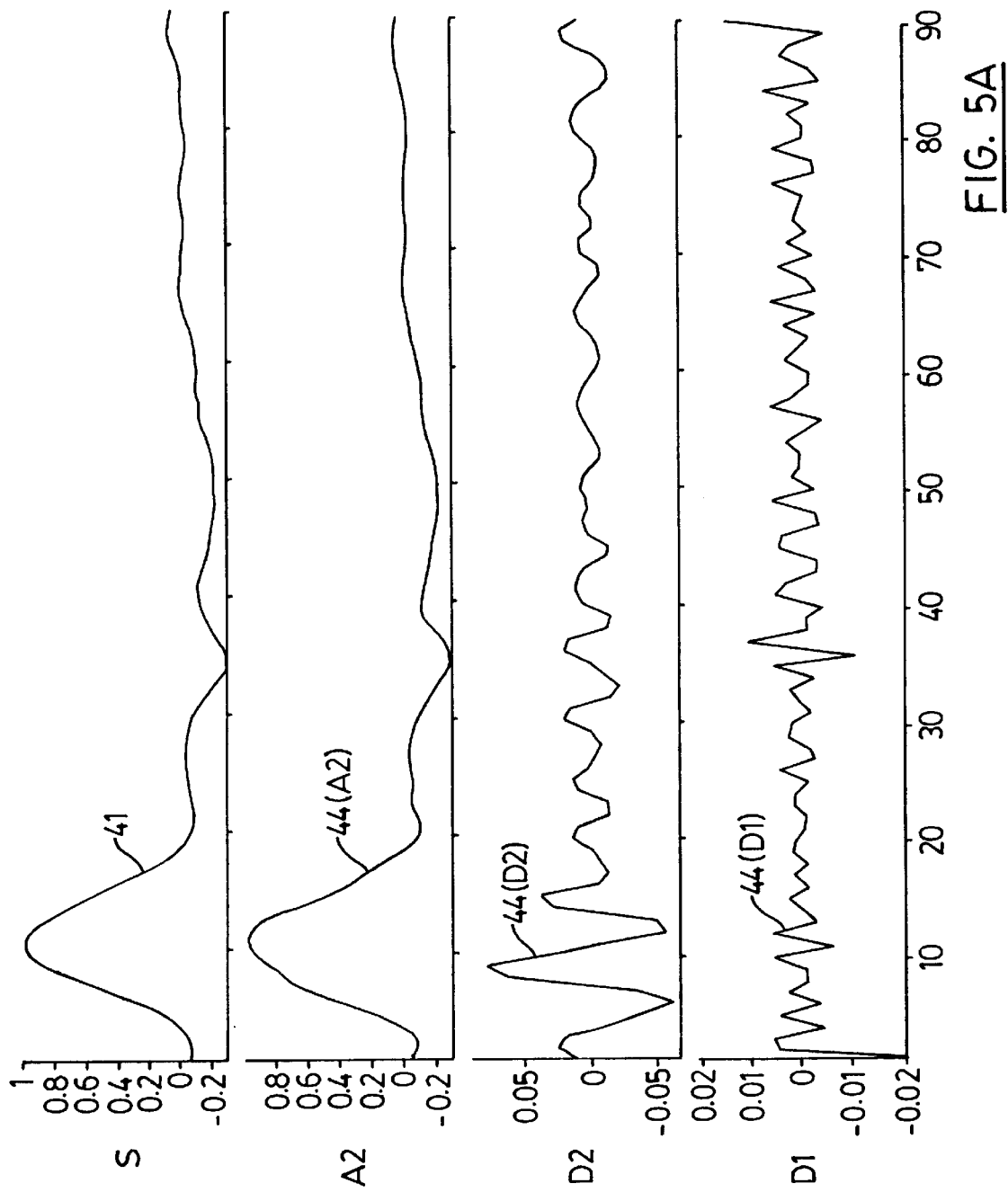
FIG. 5(a) shows in graphical form the decomposition of the normalized pressure contour signal of FIG. 4(a)
Figure 5B:
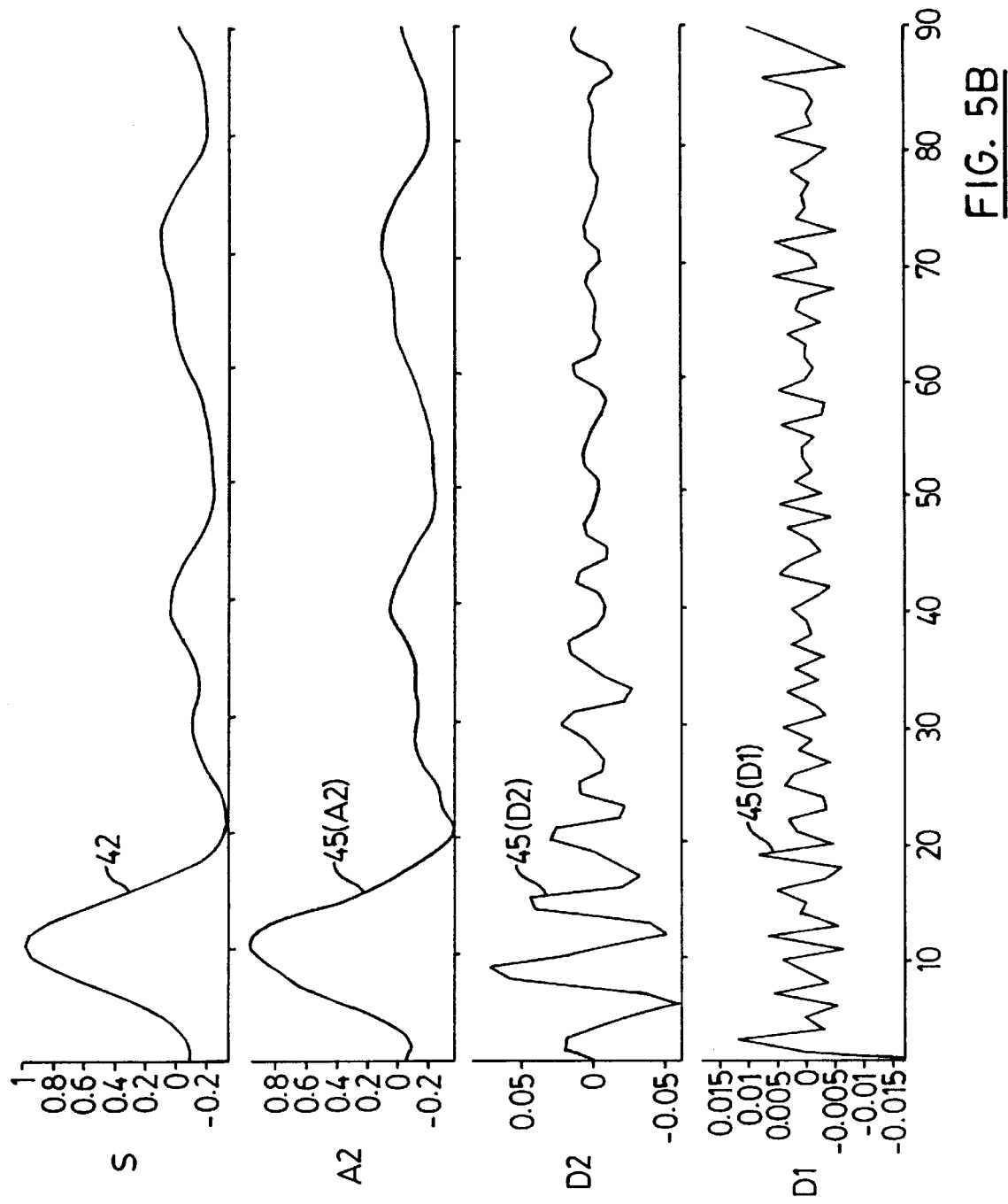
FIG. 5(b) shows in graphical form the decomposition of the normalized pressure contour signal of FIG. 4(b)

Each basis function has its own advantages and disadvantages when performing waveform analysis. In the context of the present invention, the Daubechies wavelet family is chosen as the preferred basis function for characterizing the arterial pressure pulse contour signal. The Daubechies wavelet is particularly suited for analyzing signals which have sharp features. In the preferred embodiment, a $4^{th}$ order Daubechies wavelet is used to perform a discrete transform, i.e. decomposition, on the normalized pressure pulse contour signals 40 (FIG. 4) from the time and amplitude normalization stage 32 (FIG. 3). The wavelet transform stage 34 decomposes each normalized pressure contour signal 40 into respective approximation a2 and detail functions d1 and d2. The approximation a2 and detail functions d1, d2 provide a series of wavelet coefficients which are used to identify characteristics of the patient's cardiovascular system as will be described below. As shown in FIG. 5(a), the normalized pressure contour signal 41 taken during normal breathing is transformed into an approximation signal 44(a2), first and second detail functions 44(d1) and 44(d2). Similarly, the normalized pressure contour signal 42 taken during the Valsalva maneuver is transformed into an approximation signal 45(a2), and first and second detail functions 45(d1) and 45(d2) as shown in FIG. 5(b). Similarly, the normalized pressure contour signal 43 taken when the patient was holding their breath is transformed into an approximation signal 46(a2), and first and second detail functions 46(d1) and 46(d2) as shown in FIG. 5(c).

In the preferred embodiment, the $4^{th}$ order Daubechies wavelet transform is implemented mathematically by repeatedly applying a transform matrix of the $4^{th}$ order Daubechies wavelet coefficients to the normalized pressure pulse contour signals 40.

Figure 6A:
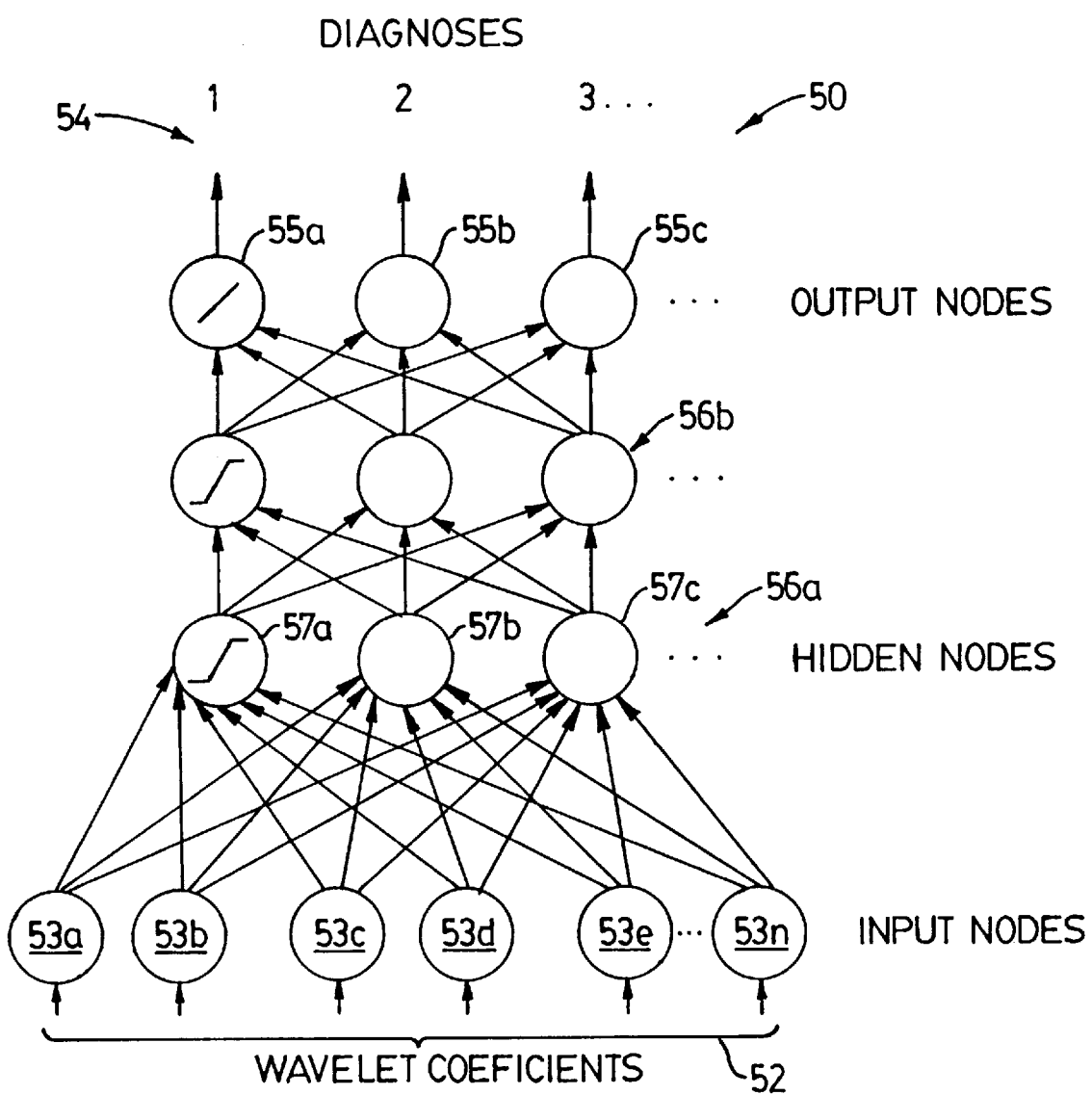
FIG. 6(a) shows a first type of neural network for the system of FIG. 1.

The output signals, i.e. wavelet coefficients, from the wavelet transform stage 34 are provided to the input of the neural network stage 36. In the context of the present invention, the principal function of the neural network 36 is to characterize cardiovascular or related illness based on the coefficients generated by the wavelet transform stage 34 for the normalized pressure contour signal 40. Artificial neural networks are described in M. T. Hagan, H. B. Demuth, M. Beale, *Neural Network Design,* Boston: PWS Publishing, 1996, and are well known to persons skilled in the art. In the context of the present system, the neural network stage 36 includes a neural network 50 comprising an input layer 52, an output layer 54 and a series of hidden layers 56 as shown in FIG. 6(a). The input layer 52 comprises a series of processing elements 53, i.e. units or nodes, shown individually as 53a, 53b, 53c . . . 53n. Similarly, the output layer 54 comprises a series of processing elements 55, shown individually as 55a, 55b, 55c . . . 55m. The hidden layers 56 also comprise a series of processing elements 57. The processing elements for the various layers are linked together by adjustable connections which are weighted. The processing capability of the neural network 50 is stored in these inter-node weights. The inter-node weights are obtained by training the neural network 50 with a plurality of training sets. As shown in FIG. 3, the training stage 35 comprises a summing element 37 and a set of training target parameters 38. The summing element 37 produces a sum-squared-error output for the neural network 36. The summing element 37 comprises a known feedback element and has one input coupled to the output of the neural network 36 and a second input for receiving the predetermined training targets 38. The output (i.e. sum-squared-error) from the summing element 37 is selectively coupled to the neural network 36 through a switch 39 which is actuated by the CPU controller 14. To train the neural network 36 an input vector, i.e. a set of wavelet coefficients, from the wavelet transform 34 is applied to the neural network 36. The summer 37 generates a sum-square-error between the output from the neural network 36 and the training target 38 corresponding to the associated characteristics of the patient's cardiovascular system, and this output is applied to the neural network 36. The training of the neural network 36 is repeated until a pre-determined error goal is reached.

The advantage of using a neural network 36 instead of a conventional computer is that the neural network 36 is able to learn from the training sets, i.e. wavelet coefficients obtained from the wavelet transform 34. Therefore, upon completion of the training, the neural network 36 is able to respond appropriately to input vectors which were not included in the training set.

Figure 6B:
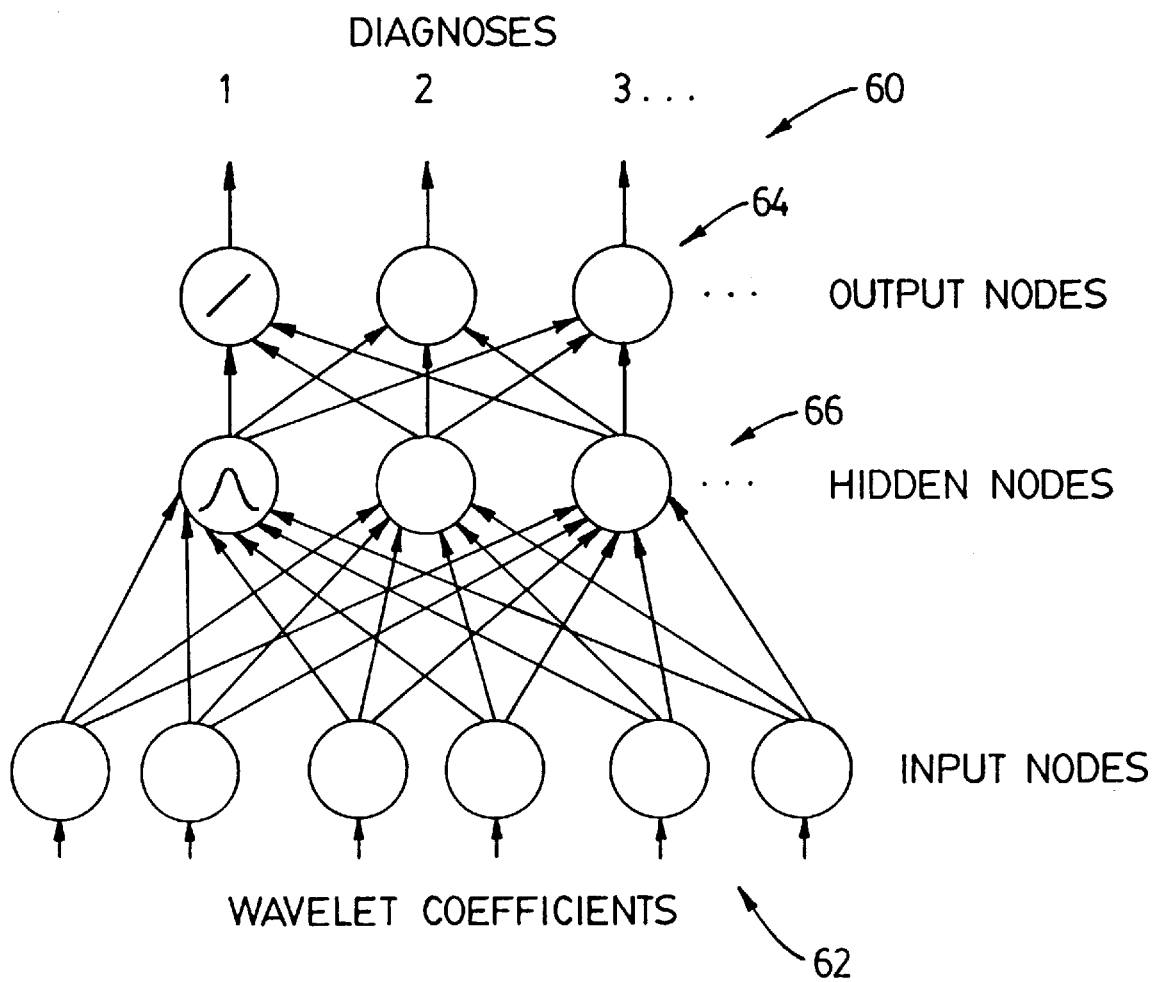
FIG. 6(b) shows a second type of neural network for the system of FIG. 1.

As will be appreciated by one skilled in the art, many known types of neural networks are available, and the suitability of each network type will vary based on the input data. In the context of the present invention, the neural network stage 36 preferably comprises a multi-layer perceptron (i.e. backpropagation) neural network 50 as shown in FIG. 6(a) or a radial basis function neural network 60 as shown in FIG. 6(b). The multi-layer perceptron neural network 50 comprises one or two hidden layers 56a and 56b. In the multi-layer perceptron neural network 50, the hidden layers 56 comprise sigmoidal activation functions and the output layer 54 comprises linear activation functions. In the preferred embodiment, the multi-layer perceptron neural network 50 is trained with a backpropagation learning algorithm.

A radial basis function neural network 60 is shown in FIG. 6(b). The radial basis function neural network 60 comprises an input layer 62, an output layer 64 and a single hidden layer 66. The processing elements 67 in the hidden layer 66 comprise Gaussian activation functions. The processing elements for the output layer 64 comprise linear activation functions. For the neural networks 50 and 60, a bias unit with a constant state of 1 is connected to all hidden and output nodes.

The input vector for both the backpropagation network 50 (FIG. 6(a)) and the radial basis functions network 60 (FIG. 6(b)) comprise coefficients of the approximation a2 and detail functions d1, d2 (FIGS. 5(a) to 5(c))) produced by the wavelet transform stage 34. Because the first level detail function d1 comprises mostly noise, i.e. information not correlated with the cardiac event from cycle to cycle, the coefficients of the detail function di are not used in the input vector to the input layer 52 or 62 of the neural network 50 or 60. Accordingly, for a level two decomposition the input vector comprises an ordered set of coefficients from the approximation function a2 and the second detail function d2. For a level three decomposition, the input vector comprises an ordered set of coefficients from the approximation function a3, and second d2 and d3 detail functions. In general, for a level "n" decomposition by the wavelet transform stage 34 (FIG. 3), the input vector will comprise an ordered set of coefficients from the approximation function an and detail functions dn, dn-1, . . . d1.

The output layer 54 (or 64) in the neural network stage 36 (FIG. 3) produces an output vector comprising a series of outputs ranging from 0 to 1. The number of nodes in the output layer 54 (or 64) corresponds to the number of abnormal conditions capable of being diagnosed by the system 10. During training of the neural network 36, the binary outputs in the output layer 54 are encoded so that each output vector will contain only one non-zero element, i.e. LOGIC 1, which corresponds to one specific abnormality derived from the coefficients produced by the wavelet transform stage 34. Accordingly, the dimension of the output vector, and therefore the output layer 54, increases with the number of abnormalities to be detected. It will be understood that the system 10 is not restricted to this specific encoding scheme. Other encoding schemes can be used, and the principal function of the neural network stage 36 (FIG. 3) is to associate a training set of input vectors with a specific abnormality encoded in the set of output vectors.

The neural network 36 is trained by taking arterial pressure pulse readings from a number of different subjects under a variety of conditions. For each condition, only a portion of the contour data vectors are used for network training. For example, in a set of approximately 50 to 100 arterial pressure contour readings from a plurality of subjects, approximately 80% of the contours are used for network training, while the remaining 20% are used for validation of network performance. As shown in FIG. 3, a sum square error element 37 is used to monitor the progress of training the neural network 36 with the 80% of pressure contour signals. Upon reaching a specified error goal, which will depend on the size of the training set, the neural network 36 is tested using the remaining 20% of contour data vectors, and by subjecting the output vector to a competitive transformation which renders the maximum element 1 and the rest 0. It will be appreciated that this testing format allows for the evaluation of the ability of the network 36 to correctly diagnose abnormalities from pulse contour vectors which were not part of the training set.

Experimental Findings

A system 10 according to the invention was employed to analyze data sets from three subjects under three conditions as described above with reference to FIGS. 4(a) to 4(c) and FIGS. 5(a) to 5(c). The first data set (examples are shown in FIGS. 4(a) and 5(a)) comprises radial arterial pulse readings obtained from the left arms of three subjects during normal breathing, i.e. sitting quietly. The second data set (FIGS. 4(b) and 5(b)) comprises radial arterial pulse readings obtained from the same three subjects during a Valsalva maneuver condition, i.e. the subject is straining by attempting to exhale against a closed glottis. The arterial pulse readings taken under these condition mimic abnormalities in which there is a reduction of cardiac output and arterial pulse pressure (which result from a drastic increase in intra-thoracic pressure and a reduction in venous return), an increase in sympathetic tone, an increase in partial pressure of carbon dioxide, and a decrease in partial pressure of oxygen and pH in the arterial blood. The third data set (FIGS. 4(c) and 5(c)) comprises radial arterial pulse readings obtained from the three same subjects with the subjects holding their breath at the end of inspiration. This maneuver produces to a lesser degree similar effects to the Valsalva maneuver, with little change in cardiac output, but an increase in mean arterial pressure as breath-holding progresses.

In accordance with the method of the present invention, the arterial pulse readings obtained under the different conditions described above are first normalized as shown in FIGS. 4(a) to 4(c). The normalized pulse contours 41 to 43 are then subjected to discrete wavelet transformation to generate the respective sets of wavelet coefficients 44 to 46 as described above with reference to FIGS. 5(a) to 5(c). Utilizing a 4th order Daubechies wavelet for the transform 34, a level 2 decomposition is used to produce corresponding wavelet coefficient data sets for each of subjects under the three conditions. The wavelet coefficient data sets are partitioned into a training set (i.e. 80%) and a testing set (i.e. 20%). The same test set is used as the input vectors for the backpropagation type neural network 50 having a single hidden layer, and for a radial basis function network 60. Each of the conditions was represented by a binary output vector: (1,0,0) for the normal condition, (0,1,0) for Valsalva maneuver, and (0,0,1) for breath holding.

It was found that both types of neural networks 50 and 60 reached the desired error goals in less than 5000 training epochs. When the testing set (20% of the original data set not used for training) was used to evaluate the performance of the system 10, a correct classification rate of greater than 95% for the three conditions was achieved for both the backpropagation 50 and radial basis function 60 neural networks. Similar results were obtained with wavelets coefficients at level 5 decomposition.

Reference is next made to FIGS. 7–10. FIG. 7(a) shows a normal high-pass filtered arterial pulse contour denoted by reference 101a for a Subject A and an arterial pulse contour 102a when Subject A is subjected to the Valsalva maneuver, and FIG. 7(b) shows a normal high-pass filtered arterial pulse contour denoted by reference 101b for a Subject B and an arterial pulse contour 102b when Subject B is subjected to the Valsalva maneuver. The Valsalva maneuver causes forced expiration against a closed glottis which increases intra-thoracic pressure and impedes venous return. This state, in turn, produces a dicrotic (i.e. twice-beating) pulse with a shortened systolic ejection. Such a condition produces an arterial pulse contour similar to that if the subject was experiencing cardiac failure, hypovolemic shock, or cardiac temponade.

Figure 7A:
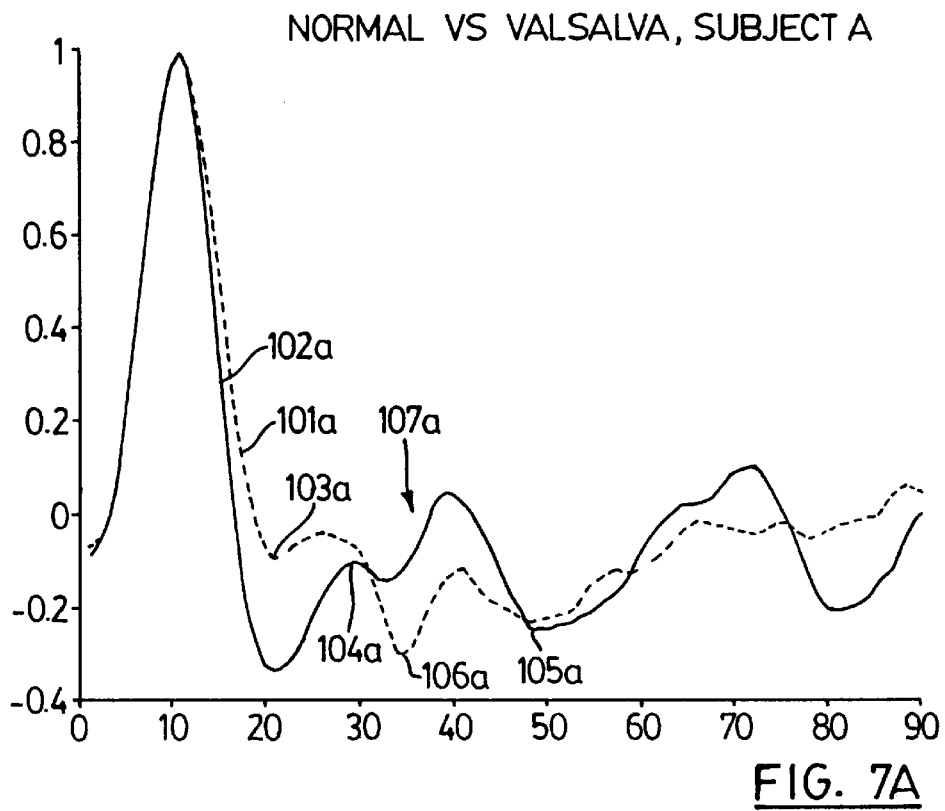
FIG. 7(a) shows arterial pressure contours obtained from a Subject A under normal conditions and during a Valsalva maneuver.
Figure 7B:
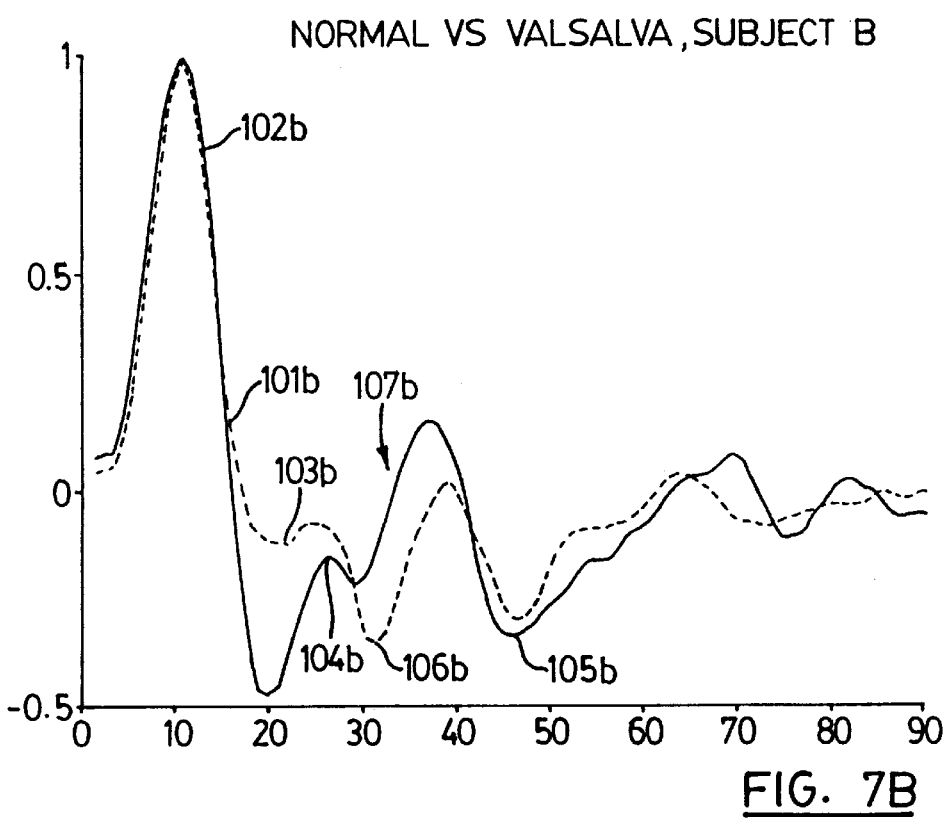
FIG. 7(b) shows arterial pressure contours obtained from a Subject B under normal conditions and during a Valsalva maneuver.
Figure 8A:
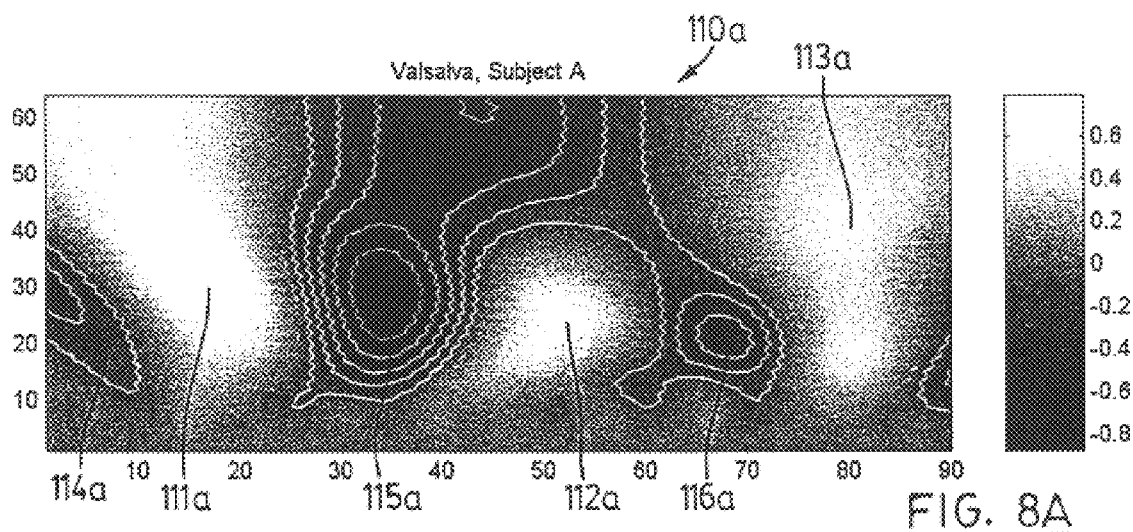
FIG. 8(a) shows a scale-cardiac cycle plot for a signature derived from the arterial pressure contours of FIG. 7(a) through the application of a wavelet transformation.
Figure 8B:
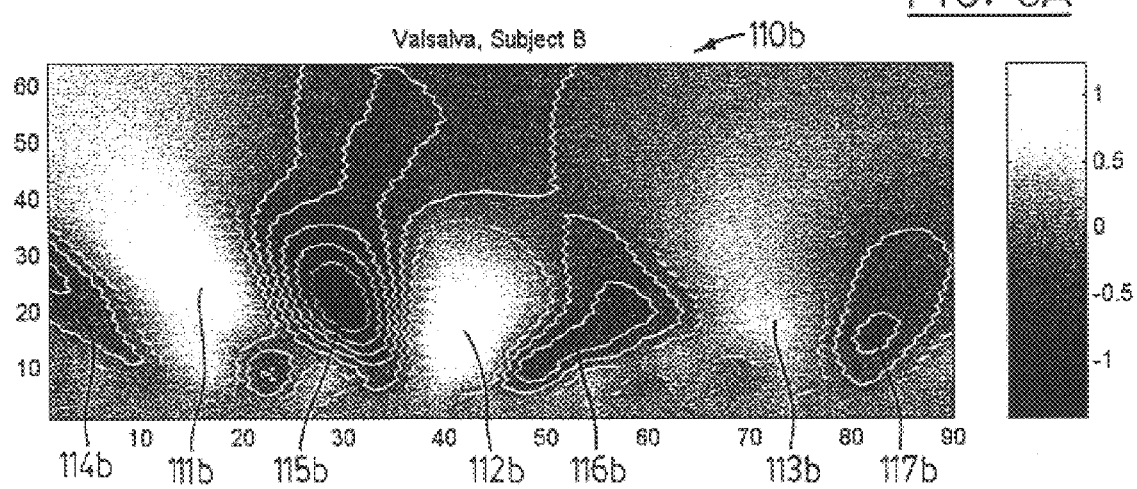
FIG. 8(b) shows a scale-cardiac cycle plot for a signature derived from the arterial pressure contours of FIG. 7(b) through the application of a wavelet transformation.

As shown in FIGS. 7(a) and 7(b), the normal arterial pulse contours 101a, 101b for Subjects A and B, respectively, are characterized by a systolic shoulder 103a, 103b followed by a dicrotic notch 106a, 106b between 300–400 milliseconds with a normalized cardiac cycle of 900 milliseconds. In contrast, the Valsalva resultant arterial pulse contours 102a and 102b exhibit respective systolic shoulders 104a and 104b and late notches 105a and 105b. As shown in FIGS. 7(a) and 7(b), the respective notches 105a, 105b which separate the twice-beating or double pulse 107a, 107b are both delayed. As described above, a signature 110 corresponding to the invariant features embedded in the normal pulse contours 101 and Valsalva resultant pulse contours 102 are generated. The signatures 110a and 110b for Subjects A and B as shown in FIGS. 8(a) and 8(b), respectively, are generated by applying the continuous wavelet transform (i.e. the $4^{th}$ order Daubechies) to the respective normal pulse contours 101 and the Valsalva resultant pulse contours 102 and subtracting the wavelet coefficients for the Valsalva pulse contours 102 from the wavelet coefficients for the normal pulse contours 101. As shown in FIGS. 8(a) and 8(b), the signatures 110 are displayed as scale-cardiac cycle plots. For Subject A in FIG. 8(a), the signature 110a comprises light regions 111a, 112a, 113a and dark regions 114a, 115a, 116a. Similarly for Subject B, the signature 10b comprises light regions 111b, 112b, 113b and dark regions 114b, 115b, 116b, 117b. The light regions 111 to 113 represent positive differences in the arterial pulse contours surrounding the systolic shoulders 103, 104 (FIGS. 7(a) and 7(b)). The dark regions 114 to 117, on the other hand, represent negative differences in the region of the dicrotic notches 106 of the normal arterial pulse contour 101.

Figure 9A:
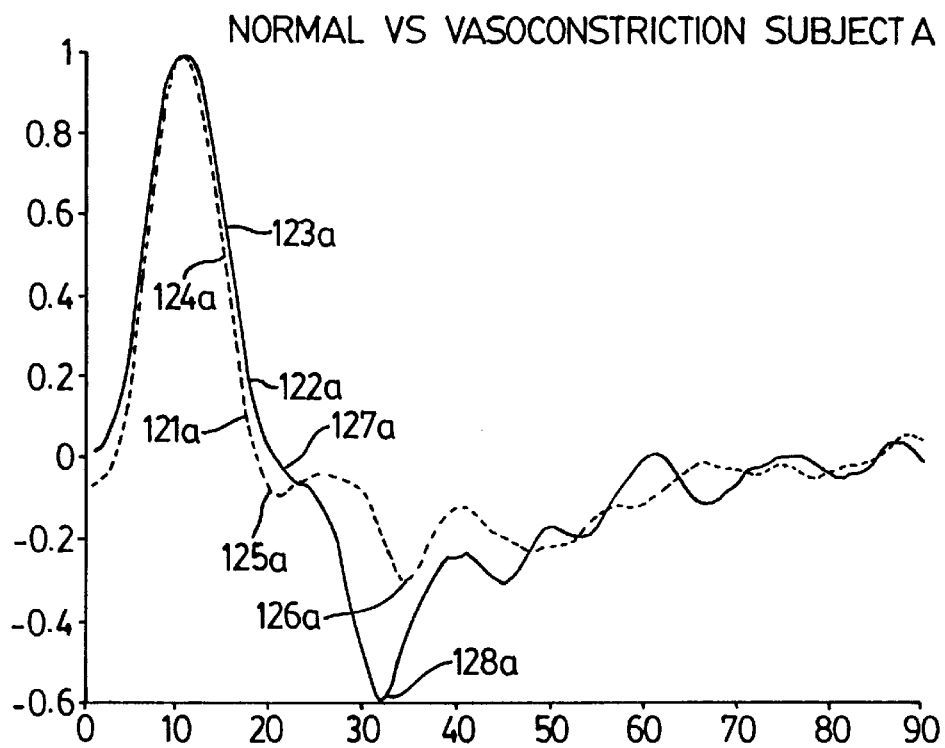
FIG. 9(a) shows arterial pressure contours obtained from Subject A under normal conditions and during a vasoconstriction condition.
Figure 9B:
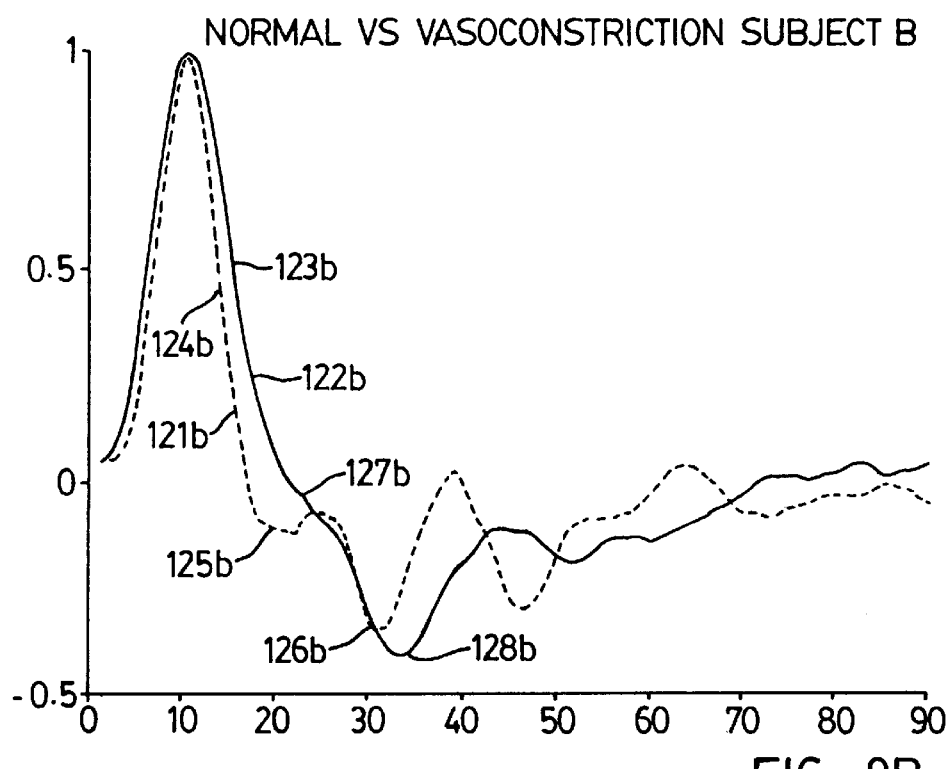
FIG. 9(b) shows arterial pressure contours obtained from Subject B under normal conditions and during a vasoconstriction condition.

Reference is next made to FIGS. 9(a) and 9(b) which show respective normal left arm arterial pulse contours 121a, 121b for Subjects A and B and arterial pulse contours 122a, 122b when the subjects experience peripheral vasoconstriction. The vasoconstriction condition is induced in the subject's arm connected to the pressure transducer 20 (FIG. 2) by exposing the subject's left hand to cold water at 0° C. for a short period. The vasoconstriction results in the amplification or augmentation of the systolic wave portion 123a, 123b relative to the diastolic wave portion as shown in FIGS. 9(a) and 9(b). The vasoconstriction also results in an increase in the duration of the systolic wave portion of the arterial pulse contour 122a, 122b when compared to the systolic wave portion 124a, 124b of the normal arterial pulse contour 121a, 121b when normalized over a cardiac cycle. In FIGS. 9(a) and 9(b), the respective systolic shoulders for the normal arterial pulse contours 121 are denoted by references 125a and 125b, and the dicrotic notches are denoted by the references 126a and 126b. For the vasoconstricted arterial pulse contours 122, the respective systolic shoulders are denoted by references 127a and 127b and the dicrotic notches are denoted by the references 128a and 128b as shown in FIGS. 9(a) and 9(b). The vasoconstriction condition produces an arterial pulse contour similar to that if the subject was experiencing severe local reflex vasoconstriction, which could be observed in people with vascular diseases of the limbs, such as Raynaud's disease.

Reference is made to FIGS. 10(a) and 10(b) which show the resulting signatures for the vasoconstricted arterial pulse contours 122. The signature for Subject A is denoted by 130a and shown in FIG. 10(a). The signature 130a is characterized by a band of negative difference wavelet coefficients 133, shown individually as 133a, 133b, 133c, which appear as dark regions in FIG. 10(a), and a series of positive difference wavelet coefficients 135, shown individually as 135a, 135b, which appear as light regions in FIG. 10(a). FIG. 10(b) shows a signature 130b for Subject B. Similarly, the signature 130b for Subject B is characterized by a band of negative difference wavelet coefficients 134, shown individually as 134a, 134b, 134c, 134d, . . . , which appear as dark regions in FIG. 10(b), and a series of positive difference wavelet coefficients 136, shown individually as 136a, 136b , which appear as light regions in FIG. 10(b). The d ark regions 133, 134 represent negative differences in the dicrotic notches 128 in the respective normal arterial pulse contours 121a, 121b (FIGS. 9(a) and 9(b)). The light regions 135, 136, on the other hand, represent positive differences surrounding the systolic shoulders 127 in the respective normal arterial pulse contours 121a, 121b (FIGS. 9(a) and 9(b)).

As described above, the wavelet coefficient sets for each of the signatures 101a, 101b (FIGS. 7(a) and 7(b)) and 121a, 121b (FIGS. 9(a) and 9(b)) are partitioned into a training set and a testing set for training and testing the neural network module 36. Upon completion of the training and testing phase, the system 11 is capable of providing a diagnosis for a Subject X based on the arterial pulse reading for that patient.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method for diagnosing cardiovascular related illness, said method comprising the steps of:
    (a) non-invasively obtaining a signal representative of a contour of an arterial pressure pulse over a single cardiac cycle and without disturbing the natural state of the artery;
    (b) extracting frequency localization information and temporal localization information from said signal;
    (c) providing the extracted information as an input to a neural network, the neural network having been trained with a plurality of training sets, each training set correlating an arterial pressure pulse contour with a known cardiovascular or related illness; and
    (d) generating an illness identification output from the neural network.

2. The method as claimed in claim 1, wherein said step of extracting comprises eliminating noise from the extracted information by performing a multi-resolution decomposition of the signal.

3. The method as claimed in claim 1, wherein said step of extracting comprises performing a wavelet transform on the signal.

4. The method as claimed in claim 1, wherein said wavelet transform comprises a Daubechies family wavelet transform.

5. The method as claimed in claim 4, wherein said wavelet transform comprises a discrete wavelet transform, and said step of extracting comprises generating an approximation function and a plurality of detail functions including performing a multi-resolution decomposition of the signal.

6. The method as claimed in claim 1, wherein said training sets are obtained from a plurality of different patients under a plurality of different conditions.

7. The method as claimed in claim 1, wherein said illness identification output comprises a plurality of illness indicators, each of the known cardiovascular or related illnesses included in the training set being associated with a respective illness indicator, and each illness indicator indicating an occurrence of the respective illness.

8. A system for detecting symptoms associated with cardiovascular related illnesses in a patient said system comprising:
    input means for receiving a signal representative of a contour of an arterial pressure pulse, said signal being obtained in a non-invasive manner from the patient and over a single cardiac cycle and without disturbing the natural state of the artery;
    information extraction means coupled to said input means for extracting frequency localization information and temporal localization information from the signal and including means for producing a localization information output signal representing a portion of the extracted information; and
    a neural network training with a plurality of training sets, each training set correlating an arterial pressure pulse contour with a known cardiovascular or related illness, said neural network including means for receiving said localization information output signal and means for producing an illness identification output signal representing a correlation between the extracted information and a cardiovascular related symptom derived from said training sets.

9. The system as claimed in claim 8, wherein said means for receiving is selectively coupled to said information extraction means for receiving only said localization information output signal.

10. The system as claimed in claim 8, wherein said information extraction means includes signal decomposition means for performing a multi-resolution decomposition of the received signal.

11. The system as claimed in claim 10, wherein said signal decomposition means comprises wavelet transformation means.

12. The system as claimed in claim 10, wherein said signal decomposition means comprises Daubechies wavelet transformation means.

13. The system as claimed in claim 8, wherein said receiving means comprises an analog-to-digital converter for generating a digitized representation of the arterial pressure pulse, said analog-to-digital converter including an input port for receiving an output signal of an arterial pressure pulse transducer, and wherein said information extraction means includes discrete wavelet transformation means coupled to said analog-to-digital converter for extracting approximation and detail function data from said received signal through a multi-resolution decomposition of the received signal, vector generation means coupled to the discrete wavelet transformation means for generating, as the localization information output signal, a vector comprising the extracted approximation and detail function data.

14. The system according to claim 8, wherein said neural network comprises a multi-layer perceptron neural network, said neural network being trained through backpropagation learning.

15. The system according to claim 8, wherein said multi-layer perceptron neural network includes a hidden layer comprising sigmoid activation functions, and an output layer comprising linear activation functions.

16. The system according to claim 8, wherein the neural network comprises a radial basis function neural network.

17. The system according to claim 16, wherein the radial basis function neural network includes an output layer comprising linear activation functions, and a hidden layer comprising Gaussian activation functions.

* * * * *